(12) United States Patent
Bassi et al.

(10) Patent No.: US 7,686,452 B2
(45) Date of Patent: Mar. 30, 2010

(54) APPARATUS AND METHOD FOR ASSESSING VISUAL SUPPRESSION

(75) Inventors: Carl J. Bassi, St. Louis, MO (US); Michael Howe, St. Charles, MO (US); Wayne Garver, St. Louis, MO (US)

(73) Assignee: The Curators of the University of Missouri, St. Louis, MO (US)

( * ) Notice: Subject to any disclaimer, the term of this patent is extended or adjusted under 35 U.S.C. 154(b) by 636 days.

(21) Appl. No.: 11/689,878

(22) Filed: Mar. 22, 2007

(65) Prior Publication Data

US 2007/0223213 A1 Sep. 27, 2007

Related U.S. Application Data

(60) Provisional application No. 60/784,579, filed on Mar. 22, 2006.

(51) Int. Cl.
*A61B 3/02* (2006.01)
(52) U.S. Cl. .................................. 351/243; 351/232
(58) Field of Classification Search ......... 351/200–203, 351/222, 232, 243
See application file for complete search history.

(56) References Cited

U.S. PATENT DOCUMENTS

| | | | |
|---|---|---|---|
| 2,262,217 A | 11/1941 | Wottring | |
| 2,986,969 A | 6/1961 | Muncheryan | |
| 3,737,217 A * | 6/1973 | Haines et al. | 351/224 |
| 4,188,097 A | 2/1980 | Holladay | |
| 4,784,483 A * | 11/1988 | Holladay et al. | 351/243 |
| 4,818,091 A | 4/1989 | Sadun et al. | |
| 4,826,308 A | 5/1989 | Sadun | |
| 6,642,502 B2 | 11/2003 | Waki | |
| 2004/0076942 A1 | 4/2004 | O'Neil et al. | |
| 2005/0010091 A1 | 1/2005 | Woods et al. | |
| 2005/0161586 A1 | 7/2005 | Rains, Jr. et al. | |

FOREIGN PATENT DOCUMENTS

| | | |
|---|---|---|
| GB | 1093232 A | 11/1967 |
| WO | 2005043224 A2 | 5/2005 |

OTHER PUBLICATIONS

Worth 4 dot test, http://en.wikipedia.org/wiki/Worth_4_dot_test, Mar. 17, 2006, 1 page, United States.

\* cited by examiner

*Primary Examiner*—Huy K Mai
(74) *Attorney, Agent, or Firm*—Senniger Powers LLP

(57) ABSTRACT

A device is used to determine the presence of and the amount (depth) of visual suppression in a subject. The device includes a first light source emitting a first light and a second light source emitting a second light. Intensities of the light sources are independently controllable. A first filter disposed over one eye of the subject allows transmission of the first light and prevents transmission of the second light. A second filter disposed over the other eye of the subject allows transmission of the second light and prevents transmission of the first light. In a method of using the device, the intensity of at least one of the first and second lights is independently controlled, wherein the difference in intensities of the first and second lights at which the lights appear to be at equal brightness to the subject determines the amount of visual suppression in the subject.

20 Claims, 4 Drawing Sheets

APPARATUS AND METHOD FOR ASSESSING VISUAL SUPPRESSION

CROSS-REFERENCE TO RELATED APPLICATION

The present application claims priority to U.S. Provisional Application No. 60/784,579 filed Mar. 22, 2006, the entirety of which is herein incorporated by reference.

FIELD OF THE INVENTION

The present invention relates generally to a device and a method for determining the presence of and the amount (depth) of visual suppression in a subject.

BACKGROUND OF THE INVENTION

Visual suppression may be characterized by a decrease in sensitivity or acuity in an eye. The decreased sensitivity may be caused by non-transmission, or poor transmission, of the optic nerve or from alterations in sensitivity in the brain. For example, deprivation of vision, strabismus (misaligned eyes), vision obstructing disorders, anisometropia or optic neuritis may cause visual suppression. There also can be unequal sensitivity between the two eyes because of changes in light transmission (e.g. a dense cataract) or a retinal abnormality in one eye.

A Worth 4-dot test is one conventional test that may be administered to a subject to determine if the subject is suppressing an eye. The Worth 4-dot test involves the use of a device with two (2) green lights, one (1) red light, and one (1) white light. A subject wears glasses having one green filter or lens over one eye (e.g., the left eye) and one red filter or lens over the other eye (e.g., the right eye). The subject is instructed to look at the white light and verbalize whether he or she can see all four dots. If, for example, the subject can see all four dots, then it may be concluded that neither eye of the subject is being suppressed. If, however, the subject can only see three lights (two green lights and the white light), then it may be concluded that the subject's right eye (i.e., the eye associated with the red filter) is being suppressed. Alternatively, if the subject can only see two lights (the red light and white light), then it may be concluded that the subject's left eye (i.e., the eye associated with the green filter) is being suppressed. Other clinical tests include assessment of the pupil and brightness sense assessment.

All of the current methods for assessing visual suppression have limitations. The Worth 4-dot test is only a qualitative test in that it can be used to determine whether an eye is being suppressed, but it cannot be used to determine the depth (i.e., the quantitative amount) of suppression. There must be a severe impairment in visual sensitivity before a change can be detected with the Worth 4-dot. Pupil assessment does not necessarily correlate with actual visual function. Brightness sense disparity has limitations because it requires only using one eye at a time that may not accurately assess vision with both eyes open. A system or apparatus that could be used to determine the depth of suppression would allow a medical professional to select appropriate visual therapy and determine the progress of the therapy by periodically re-testing the subject.

SUMMARY OF THE INVENTION

In one aspect of the present invention, a device for determining the depth of visual suppression in a subject comprises a first light source emitting light having a first spectral output. A second light source spaced from the first light source emits a light having a different second spectral output that does not overlap the first spectral output. Intensities of the light emitting from the first and second light sources are independently controllable.

In another aspect, a kit for determining the depth of visual suppression in a subject comprises a device including a first light source emitting a first light and a second light source spaced from the first light source emitting a second light. Intensities of the first light and the second light are independently controllable. A first filter for being placed over one eye of the subject allows transmission of the first light therethrough while substantially preventing transmission of the second light therethrough. A second filter for being placed over the other eye of the subject allows transmission of the second light therethrough while substantially preventing transmission of the first light therethrough.

In yet another aspect, a method of determining depth of visual suppression in a subject comprises displaying a first light, and displaying a second light. Each of the first and second lights has an intensity. A first filter is disposed over one eye of the subject. The first filter is adapted to allow transmission of the first light therethrough and substantially prevent the transmission of the second light therethrough. A second filter is disposed over the other eye of the subject. The second filter is adapted to allow transmission of the second light therethrough and substantially prevent the transmission of the first light therethrough. The intensity of at least one of the first and second lights is independently controlled. The intensities of the first and second lights at which the lights appear to be at equal brightness to the subject determine the amount of visual suppression in the subject.

BRIEF DESCRIPTION OF THE DRAWINGS

Corresponding reference characters indicate corresponding parts throughout the drawings.

DETAILED DESCRIPTION OF THE DRAWINGS

Figure 1:
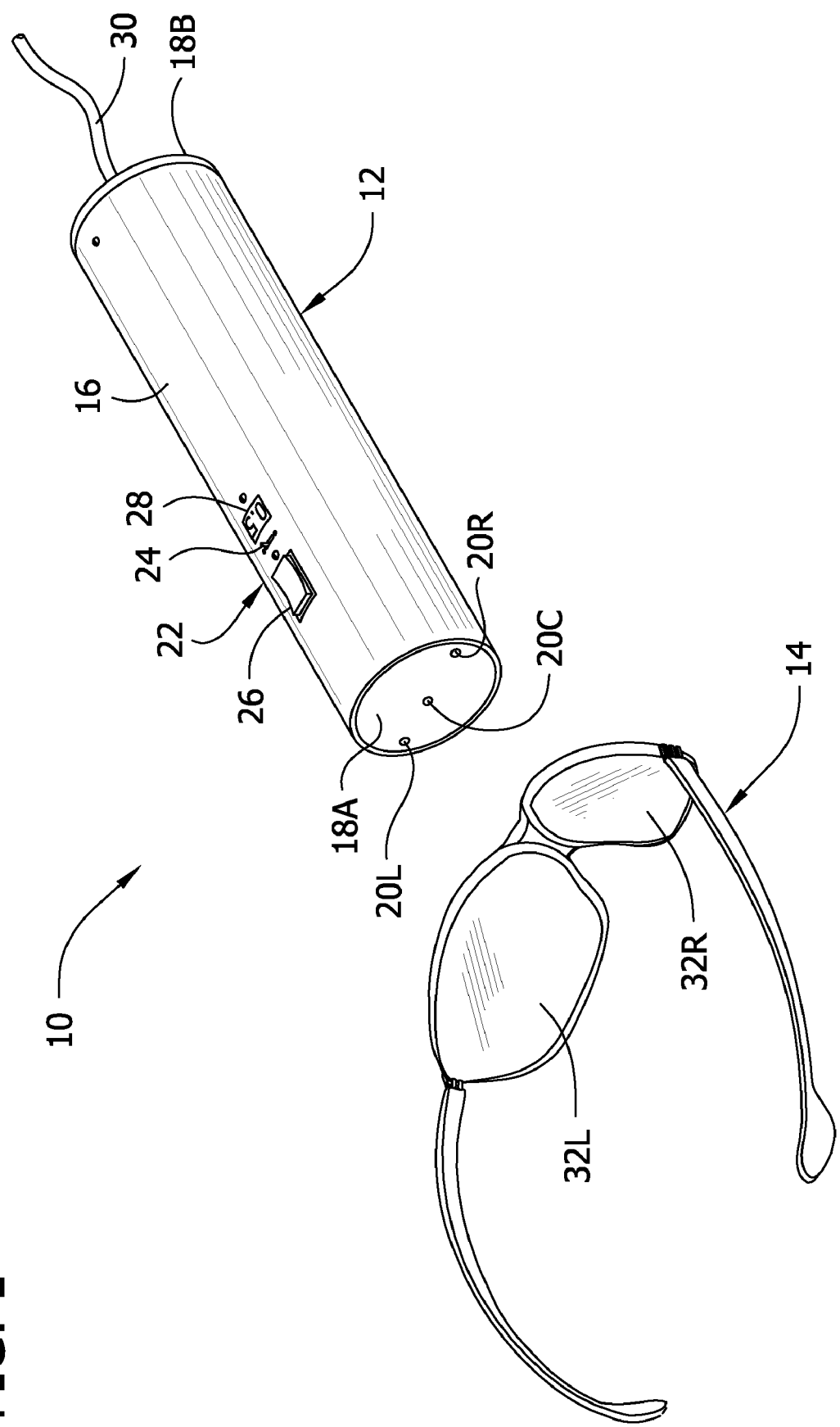
FIG. 1 is a perspective view of a kit for use in determining the depth of visual suppression in a subject including a light emitting apparatus and a pair of filter glasses.

Referring now to the drawings, and in particular to FIG. 1, a kit for determining the depth or amount of visual suppression in a subject is generally indicated at 10. The kit 10 comprises a light emitting apparatus, generally indicated at 12, and a pair of glasses, generally indicated at 14, both of which are described in detail below.

Figure 2:
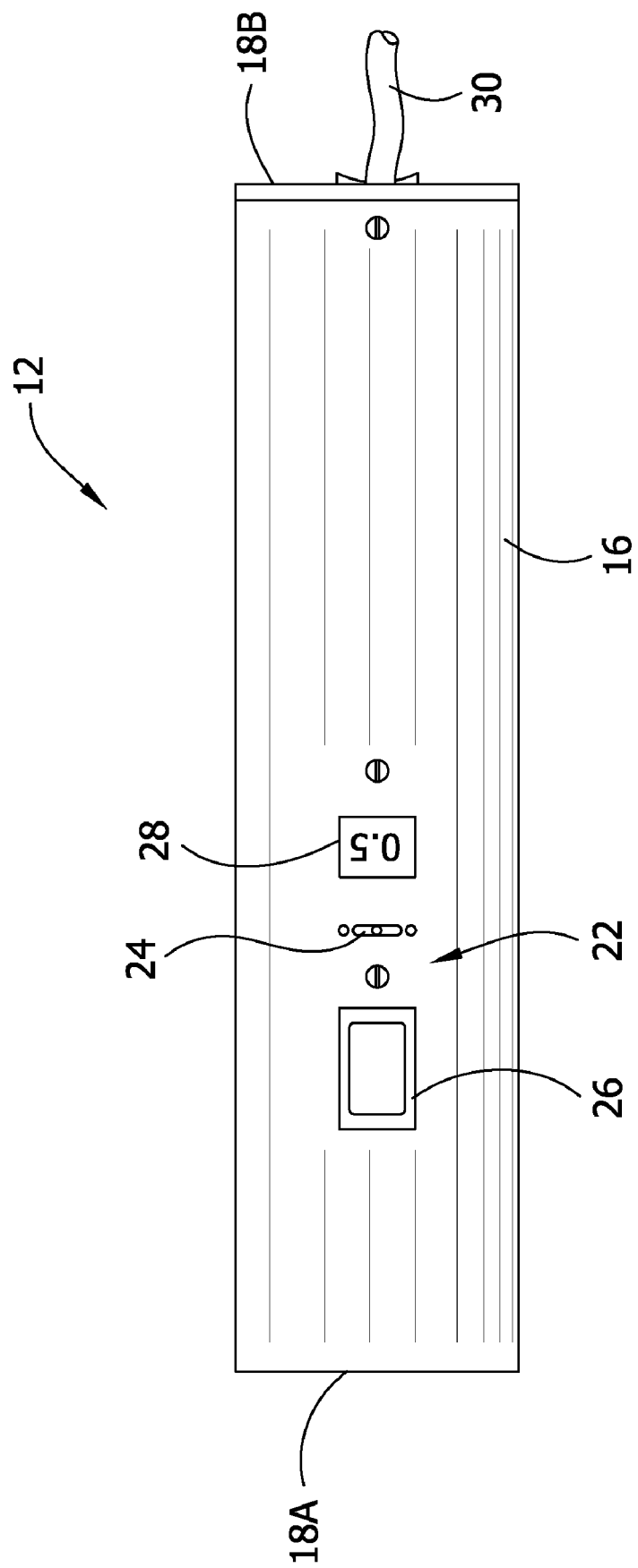
FIG. 2 is a top plan view of the light emitting apparatus.
Figure 3:
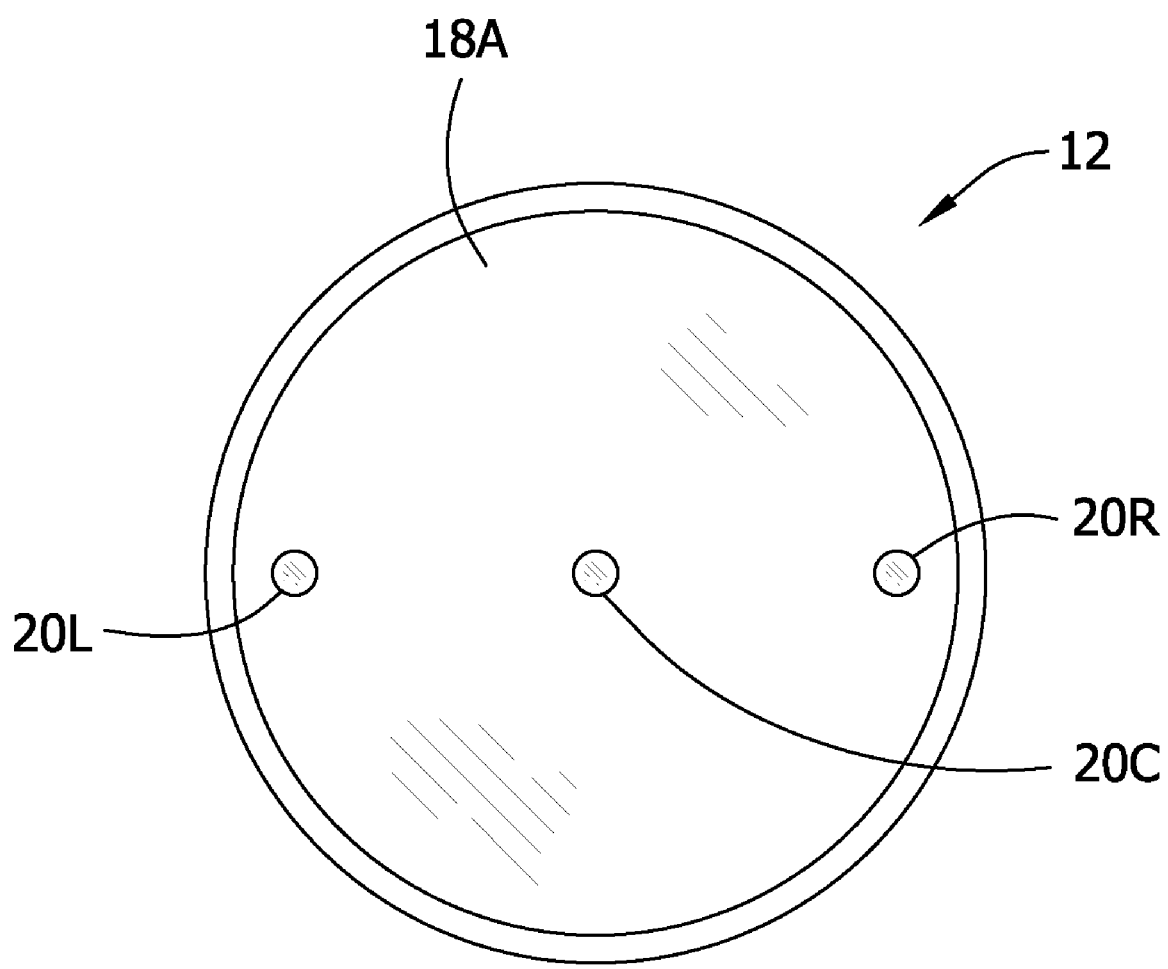
FIG. 3 is a front elevational view of the light emitting apparatus.

Referring to FIGS. 1-3, the light emitting apparatus includes a housing 16 that is generally cylindrical, much like the shape of a flashlight, having opposite generally circular ends 18A, 18B. Three light emitting diodes (LEDs) 20L, 20C, 20R are disposed at one of the ends 18A of the housing 16. The LEDs 20L, 20C, 20R are generally aligned horizontally, although other configurations are within the scope of this invention. The left LED 20L (broadly, a first light source) may be configured to emit light having a first spectral output with a peak emission wavelength corresponding to green light, and the right LED 20R (broadly, a second light source) may be configured to emit light having a second spectral output with a peak emission wavelength corresponding to red light. The first and second spectral outputs of the light emitting from the respective LEDS do not overlap in this embodiment. That is, the first spectral output includes a range of wavelengths that does not overlap a range of wavelengths of the second spectral output. The middle or center light 20C (broadly, a third light source) may be configured to emit white light. It is understood that the terms "left" and "right" refer only to the orientation of the lights as depicted in the drawings and are not meant to be limiting in any way. The configuration of the light colors may be other than described. As explained in more detail below, the LEDs 20L, 20C, 20R may be configured to emit light having a spectral output with a peak emission wavelength other than specified without departing from the scope of this invention. It is also understood that the light emitting apparatus 12 may include devices other than LEDs that emit light having different spectral outputs.

The light emitting apparatus 12 also includes an intensity device, generally indicated at 22, for independently controlling intensities of the light emitting from the left and the right LEDs, 20L, 20R, respectively. That is, the intensity device 22 allows an operator to selectively control (e.g., increase and/or decrease) the intensity of the light emitting from either the left or the right LEDs 20L, 20R, respectively, without affecting the intensity of the other light. (The intensity of the light emitting from the center light source 20C may remain constant.)

Figure 4:
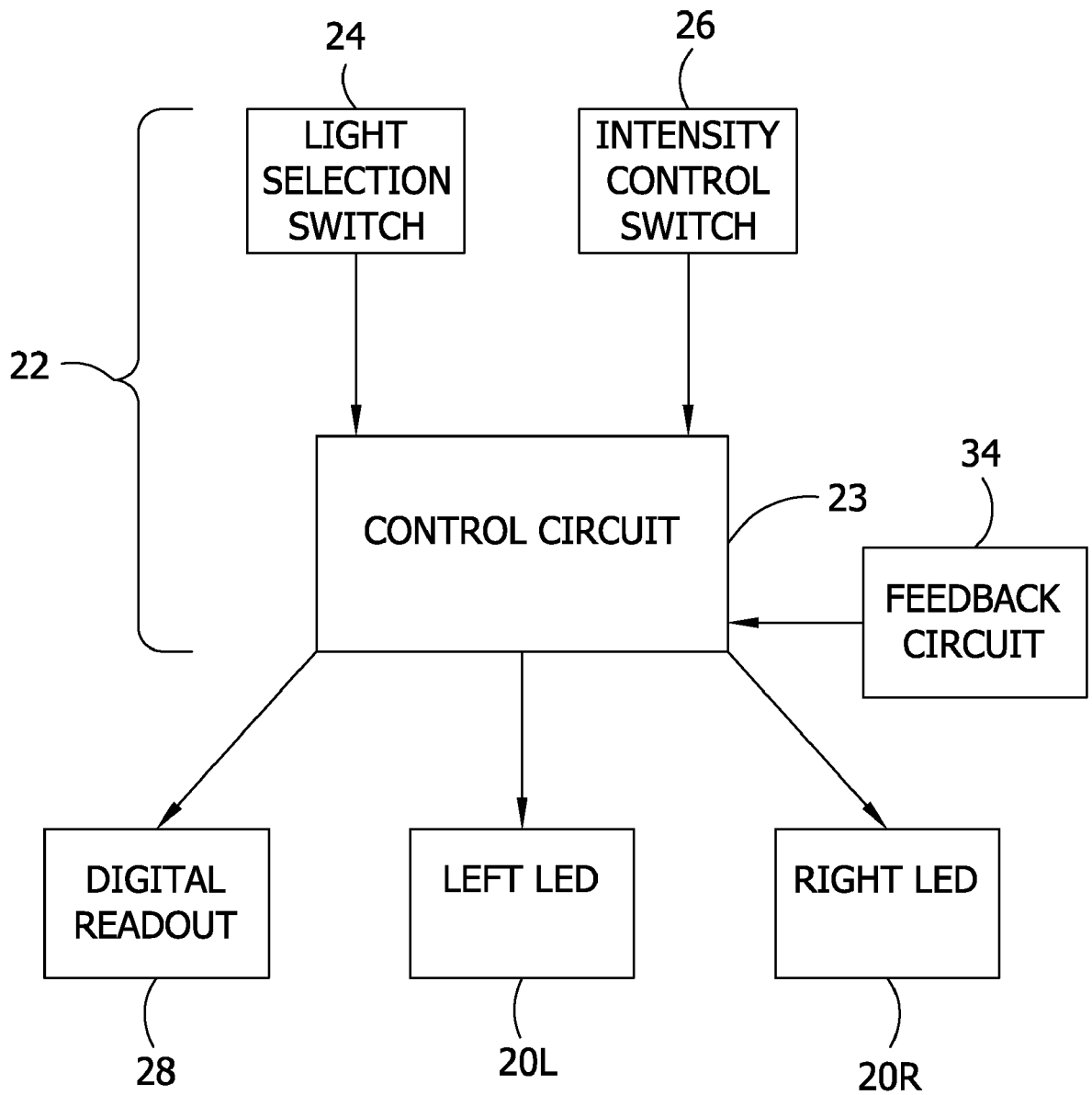
FIG. 4 is a schematic illustrating communication between a control circuit of the light emitting apparatus and components of the light emitting apparatus.

Referring to FIGS. 1, 2 and 4, the intensity device 22 of one embodiment comprises a control circuit 23 (FIG. 4) controlling the intensity (i.e., the output) of the LEDs 20L, 20C, 20R, a light selection switch 24 to select the light 20L, 20R whose intensity will be controlled by the circuit, and an intensity control switch 26 to actuate the increase and/or decrease of the intensity of the selected light by the circuit. The light selection switch 24 and the intensity control switch 26 may be broadly referred to as input interfaces. A digital readout 28 of log units of intensity (broadly, an output interface) is disposed on the housing 16.

In one embodiment, the light selection switch 24 is a sliding switch that is selectively movable between a first position, in which operation of the intensity control switch 26 controls the intensity of only the left LED 20L, and a second position, in which operation of the intensity control switch controls the intensity of only the right LED 20R. The light selection switch 24 may be operable in other ways suitable for allowing the operator to selectively and independently control the intensities of the light emitting from the left and right LEDs 20L, 20R, respectively.

The intensity control switch 26 of one embodiment is a rocker switch, whereby depressing one end of the switch actuates an increase in the intensity of the selected LED 20L, 20R while depressing the opposite end actuates a decrease in the intensity of the selected LED. Other types of switches suitable for selectively increasing or decreasing the intensity of the selected LED 20L, 20R are within the scope of this invention. It is also contemplated that the light emitting apparatus 12 may not include a light selection switch 24, but instead may include separate intensity control switches 26 for each LED 20L, 20R. Other ways of independently controlling intensities of the LEDs 20L, 20R are within the scope of this invention.

The control circuit 23, when actuated by the intensity control switch 26, either increases or decreases the intensity of the selected LED 20L, 20R. The control circuit 23 may be pre-set to increase and decrease the intensity of the selected LED 20L, 20R by between about 0.05 log units and 1.0 log units and in one embodiment by about 0.1 log units. The base intensity (i.e., the intensity at which the light is being exponentially increased) may be, for example, about 2 millilux. The base intensities of the first and second lights 20L, 20R are set to be perceptually equivalent in brightness when viewed through the glasses 14. In one embodiment, the control circuit 23 changes the intensity of the selected LED 20L, 20R at a rate of 0.1 log units per 0.5 seconds. Thus, for example, depressing the intensity control switch 26 for 1 second will increase (or decrease) the intensity by 0.2 log units. The range of net values for the log units may be between about 0.0 log units and about 3.0 log units.

Because LEDs in general typically cannot produce light below about 20 millilux (i.e., the minimum light intensity is about 20 millilux), the control circuit 23 may be pulse-driven to produce an average intensity of light over time that is less than the minimum light intensity of the LED of 20 millilux. The pulse-driven circuit 23 effectively pulses the LED 20L, 20R such that it is turned on at maximum intensity for a period of time and then turned off for a period of time. For example, the average intensity of the light will equal one-half of the maximum intensity when the LED is turned off and on for the same period of time. The pulse driven circuit may be set at a rate greater than 50 Hz to the LEDs so that the light does not appear to flicker. The control circuit 23 may be a pulse-driven circuit of the type known in the art. Another reason for pulsing the LED is to maintain a consistent spectral output as a function of the light intensity. This feature is used to maintain measurement accuracy at all intensities.

The light emitting apparatus 12 is powered via an electrical cord 30 configured to electrically connect to a standard electrical outlet. The apparatus may be powered in other ways, such as by batteries or other power sources, without departing from the scope of this invention.

The light emitting apparatus 12 may be relatively small; for example, a cross-sectional diameter may be between about 1.00 in (2.54 cm) and about 10.00 in (25.4 cm), and more specifically about 1.75 in (4.45 cm). Moreover, the length of the apparatus 12 may be between about 1.00 in (2.54 cm) and about 12.00 in (30.48 cm), and more specifically about 7.25 in (18.42 cm). The relatively small size of the apparatus 12 allows for apparatus to be easily transported to different locations.

The light emitting apparatus 12 may include other features not shown in the drawings to direct the attention of younger children to the lights. For example, the apparatus 12 may include faceplates (not shown) for attaching to the end of the housing to facilitate the attention of young children. Sounds and flashing lights may also be incorporated. Other features are within the scope of this invention.

Referring back to FIG. 1, the pair of glasses 14 of the illustrated embodiment comprises a left filter 32L (broadly, a first filter) or lens for placement over the left eye of the subject and a right filter 32R (broadly, a second filter) or lens for placement over the right eye of the subject. Broadly, the left filter 32L is configured to allow transmission of the light emitting from one of the LEDS (e.g., the left LED 20L) therethrough and to prevent the transmission of the light emitting from the other of the LEDs (e.g., the right LED 20R) therethrough. The right filter 32R is configured to allow transmission of the light emitting from one of the LEDS (e.g., the right LED 20R) therethrough and to prevent the transmission of the light emitting from the other of the LEDs (e.g., the left LED 20L) therethrough. In the present embodiment, the left filter 32L has a bandpass that matches the spectral output of the left LED 20L, and the right filter 32R has a bandpass that matches the spectral output of the right LED 20R. For example, the left filter 32L may be a green filter, and the right filter 32R may be a red filter. Other ways of positioning filters 32L, 32R over the eyes of the subject, besides the use of the glasses 14, are within the scope of this invention.

As explained in more detail below, red and green lights and red and green filters are suitable for this invention because the red filter effectively blocks (i.e., filters out) the green light (shorter wavelengths) and only passes the red light (longer wavelengths), and the green filter effectively blocks (i.e., filters out) the red light and only passes the green light. Other colors that produce similar results may be used within the scope of this invention.

Referring to FIG. 4, the light emitting apparatus 12 includes an ambient light feedback circuit 34 for measuring ambient light intensity. The feedback circuit 34 may include an ambient light sensor, such as a photodiode. The ambient light feedback circuit 34 is configured to send an ambient output signal indicative of the ambient light levels to the control circuit 23. The control circuit is adapted to adjust the intensities of the LEDs 20L, 20R, 20C based on the measured ambient light intensity so that the test may be accurately performed in rooms or environments having different ambient light intensities. For example, the control circuit 23 may increase the intensities of the LEDs 20L, 20R proportionally when the apparatus is being used in a well-lit room, and would decrease the light intensities proportionally when the apparatus is being used in a darken room. At the onset of the test, the ambient light feedback circuit 34 sends the ambient output signal indicative of the ambient light intensity to the control circuit 23. Using the ambient light signal, the control circuit 23 sets the initial light intensities of the LEDs 20L, 20R, 20C. During the test, as the intensity of one of the LEDs 20L, 20R is changed, the control circuit 23 maintains the correct intensity ratio between the LEDs to ensure the accuracy of the test.

The kit 10 is used to test whether the subject is visually suppressing an eye (e.g., either the left or right eye) and the depth or extent to which the eye is being suppressed. The following exemplary test uses a left LED 20L emitting a green light 20L and a right LED emitting a red light 20R for the light emitting apparatus 12 and a green left filter 32L and a red right filter 32R for the glasses 14. The test may be performed in a dim room. The glasses 14 are placed on the subject. The distance between the subject and the light emitting apparatus 12 may be about 3 feet. The operator can hold the light emitting apparatus 12 or have it resting or mounted on a surface or other device. The apparatus 12 is turned on so that all three LEDs 20L, 20C, 20R are emitting light that appear to be the same intensity when viewed through the glasses 14. The subject is instructed to focus or direct his/her eyes on the center, white light 20C. The subject is instructed to verbalize or otherwise communicate whether the green and red LEDs 20L, 20R appear to be at equal brightness. If the subject communicates that the LEDs 20L, 20R are emitting light of equal brightness, then it may be concluded that the subject is not visually suppressing an eye.

If, however, the subject communicates that the light emitting from the LEDs 20L, 20R are not of equal brightness or if the subject can only see two lights (i.e., the white light 20C and one of the colored lights), then it may be concluded that the subject is suppressing an eye. If the subject communicates that he or she cannot see the green light emitting from the left LED 20L, for example, or the green light appears less bright than the red light emitting from the right LED 20R, then it may be concluded that the subject is suppressing the left eye. If the subject communicates that he or she cannot see the red light emitting from the right LED 20R, for example, or the red light appears less bright than the green light emitting from the left LED 20L, then it may be concluded that the subject is suppressing the right eye.

Using the information communicated by the subject, the operator moves the light selection switch 24 to the select the appropriate LED emitting light that cannot be seen or appears to be less bright to the subject. The operator then operates the intensity control switch 26 (e.g., depresses the rocker switch) to increase the intensity of the light emitting from the selected LED 20L, 20R, and the subject is instructed to communicate when the lights appear to be of equal brightness. The operator controls the rate at which the intensity of the light emitting from the selected LED 20L, 20R is increased, and the operator is able to decrease the intensity at the commands of the subject or if the subject is uncertain at what intensity the lights appear to be of equal brightness. When the subject communicates that the light emitting from the LEDs 20L, 20R are of equal brightness, the operator collects the numerical data in log units from the digital readout 28.

In another example, the subject operates the apparatus 12 independent of the operator and performs the above steps himself or herself. Other ways of operating the apparatus 12 are within the scope of the invention.

The intensity of the light emitting from the selected LED 20L, 20R at which the lights appear to be of equal brightness corresponds directly to the depth of suppression in the subject. For example, it may be determined that a subject with a numerical readout of 2.0 log units probably has greater visual suppression than a subject having a numerical readout of about 0.5 log units. Accordingly, because the log unit readout corresponds to the depth of suppression, an eye care professional, such as an optometrist or an ophthalmologist, may be able to prescribe visual therapy or patching an eye based on the depth of the suppression. Moreover, the results and/or progress of the visual therapy may be determined using the kit. For example, if the subject communicated that the lights appeared to be at equal brightness at 2.0 log units and after visual therapy the subject communicates that the lights are of equal brightness at 1.5 log units, then the medical professional may conclude that the visual therapy is progressing either adequately or inadequately, and the subject may continue with the therapy or switch to a different type of therapy, respectively.

It is understood that the test may be performed in other ways. For example, the LEDs 20L, 20R may be set at a high initial intensity (e.g., 3.0 log units) and the operator may decrease the intensity of the light that appears brightest until the lights are of equal brightness. Using the same example given above, if the green light emitting from the left LED 20L appears brightest, then the subject is probably suppressing his right eye. Accordingly, the operator would select the left LED 20L to decrease its light intensity until the lights appear to be of equal brightness. The readout 28 at which the lights 20L, 20R appear at equal brightness may correspond directly to the depth of suppression of the subject's right eye. Other ways of using the kit 10 to determine the depth of visual suppression in a subject are within the scope of this invention.

In another embodiment of the present invention, the general structure of the components of the kit is the same as the embodiment of FIGS. 1-4; therefore, corresponding parts will be indicated by corresponding reference numerals. In this embodiment, the first light emitting from the left LED 20L (broadly, the first light source) is polarized in a first plane and the second light emitting from the right LED 20R (broadly, the second light source) is polarized in a different second plane. For example, a first polarizing filter may be associated with the left LED 20L so that the first light is polarized in the first plane, and a different second polarizing filter may be associated with the right LED 20R so that the second light is polarized in the second plane that is generally orthogonal to the first plane. The left filter 32L of the glasses 14 is polarized to match the light emitting from one of the LEDs 20L, 20R (e.g., the left LED 20L) to allow transmission of the polarized light from the LED to the subject's left eye and prevent the transmission of the light from the other LED (e.g., the right LED 32R) to the subject's left eye. Conversely, the right filter 20R is polarized to allow the transmission of the polarized light from the other LED (e.g., the right LED 32R) to the subject's right eye and prevent the transmission of the light from the first LED (e.g., the left LED 32L) to the subject's right eye. As will be understood by those in the art, the testing procedure for the kit of this embodiment would work in a substantially similar manner as the above-described procedure for the kit of the previous embodiment.

When introducing elements of the present invention or the illustrated embodiment(s) thereof, the articles "a", "an", "the" and "said" are intended to mean that there are one or more of the elements. The terms "comprising", "including" and "having" are intended to be inclusive and mean that there may be additional elements other than the listed elements.

As various changes could be made in the above constructions, products, and methods without departing from the scope of the invention, it is intended that all matter contained in the above description and shown in the accompanying drawings shall be interpreted as illustrative and not in a limiting sense. Further, all dimensional information set forth herein is exemplary and is not intended to limit the scope of the invention unless stated otherwise.

What is claimed is:

1. A device for determining depth of visual suppression in a subject, comprising
    a first light source emitting light having a first spectral output, and a second light source spaced from the first light source and emitting light having a different second spectral output that does not overlap the first spectral output, wherein intensities of the light emitting from the first and second light sources are independently controllable.

2. A device as set forth in claim 1 further comprising a control circuit for selectively and independently changing the intensities of the first and second light sources.

3. A device as set forth in claim 2 wherein the control circuit is configured to increase and decrease the intensities of the light source by between about 0.05 log units and about 1.0 log units.

4. A device as set forth in claim 3 wherein the control circuit comprises a pulse-driven circuit.

5. A device as set forth in claim 2 further comprising an input interface for controlling the control circuit.

6. A device as set forth in claim 5 wherein the input interface includes an intensity control switch in communication with the control circuit to independently actuate change in light intensity of at least one of the light sources.

7. A device as set forth in claim 6 further comprising a light selection switch for selection of one of the light sources to be controlled by the intensity control switch.

8. A device as set forth in claim 5 further comprising an output interface for communicating the intensity of at least one of the light sources to a user.

9. A device as set forth in claim 1 further comprising a feedback circuit to measure ambient light levels and to provide a feedback signal to the control circuit indicative of the ambient light level.

10. A device as set forth in claim 1 further comprising a third light source emitting a white light.

11. A kit for determining depth of visual suppression in a subject, comprising
    a device including a first light source emitting a first light and a second light source spaced from the first light source emitting a second light, wherein intensities of the first light and the second light are independently controllable,
    a first filter for being placed over one eye of the subject, wherein the first filter allows transmission of the first light therethrough while substantially preventing transmission of the second light therethrough and
    a second filter for being placed over the other eye of the subject, wherein the second filter allows transmission of the second light therethrough while substantially preventing transmission of the first light therethrough.

12. A kit as set forth in claim 11 wherein the first filter constitutes a first lens of a pair of glasses, and the second filter constitutes a second lens of the same pair of glasses.

13. A kit as set forth in claim 12 wherein the first light has a first spectral output and the second light has a different second spectral output that does not overlap the first output.

14. A kit as set forth in claim 12 wherein the first spectral output has a peak emission wavelength corresponding to green light, and wherein the second spectral output has a peak emission wavelength corresponding to red light.

15. A kit as set forth in claim 11 wherein the first light is polarized in a first plane and the second light is polarized in a different second plane that is generally orthogonal to the first plane.

16. A kit as set forth in claim 11 wherein the device further includes a third light source emitting a white light.

17. A method of determining a depth of visual suppression in a subject, comprising
    displaying a first light,
    displaying a second light, each of the first and second lights having an intensity,
    disposing a first filter over one eye of the subject, wherein the first filter is adapted to allow transmission of the first light therethrough and substantially prevent the transmission of the second light therethrough,
    disposing a second filter over the other eye of the subject, wherein the second filter is adapted to allow transmission of the second light therethrough and substantially prevent the transmission of the first light therethrough,
    independently controlling the intensity of at least one of the first and second lights, wherein the intensities of the first and second lights at which the lights appear to be at equal brightness to the subject determine the amount of visual suppression in the subject.

18. A method as set forth in claim 17 wherein the first light has a first spectral output and the second light has a different second spectral output that does not overlap the first spectral output.

19. A method as set forth in claim 17 wherein the first light is polarized in a first plane and the second light is polarized in a different second plane that is generally orthogonal to the first plane.

20. A method as set forth in claim 17 further comprising displaying a third light that is white.

* * * * *